(12) United States Patent
Nicholas et al.

(10) Patent No.: US 10,462,876 B2
(45) Date of Patent: Oct. 29, 2019

(54) LIGHT EMITTING DIODE SENSOR DEVICE INCLUDING A CONTOURED STRUCTURE

(71) Applicant: ABB Schweiz AG, Baden (CH)

(72) Inventors: Nolan W. Nicholas, Granby, CT (US); Saumya Sharma, New Britain, CT (US); Yixin Liu, New Britain, CT (US)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 15/609,879

(22) Filed: May 31, 2017

(65) Prior Publication Data
US 2018/0347797 A1    Dec. 6, 2018

(51) Int. Cl.

| | |
|---|---|
| *G01J 1/58* | (2006.01) |
| *G01J 3/02* | (2006.01) |
| *H05B 33/08* | (2006.01) |
| *G01J 1/30* | (2006.01) |
| *H05B 37/02* | (2006.01) |
| *H01L 27/144* | (2006.01) |

(52) U.S. Cl.
CPC .............. *H05B 33/089* (2013.01); *G01J 1/30* (2013.01); *H01L 27/144* (2013.01); *H05B 33/0851* (2013.01); *H05B 37/0209* (2013.01)

(58) Field of Classification Search
CPC ...... F21V 23/0457; G01J 1/30; H01L 27/144; H05B 33/0851; H05B 33/089; H05B 37/0209
USPC ............................................. 257/79; 438/22
See application file for complete search history.

(56) References Cited

U.S. PATENT DOCUMENTS

| | | |
|---|---|---|
| 4,564,756 A | 1/1986 | Johnson |
| 5,035,508 A | 7/1991 | Carter et al. |
| 6,608,360 B2 | 8/2003 | Starikov et al. |
| 7,042,341 B2 | 5/2006 | McMahon |
| 7,052,180 B2 | 5/2006 | Shih |

(Continued)

OTHER PUBLICATIONS

King-Tong Lau, Susan Baldwin, Martina O'Toole, Roderick Shepherd, William J Yerazunis, Shinichi Lzuo, Satoshi Ueyama, and Dermot Diamond; Mitsubishi Electric Research Laboratories, Cambridge, MA, USA; Advanced R&D Center, Japan: "A Low-cost Optical Sensing Device Based on Paired Emitter-detector Light Emitting Diodes"; 2005; 19 pages; Cambridge, Massachusetts.

(Continued)

*Primary Examiner* — Didarul A Mazumder
(74) *Attorney, Agent, or Firm* — Taft Stettinius & Hollister LLP; J. Bruce Schelkopf

(57) ABSTRACT

A light emitting diode (LED) sensor including a first LED device disposed on a support and configured to emit a radiation, and a second LED device disposed on the support and configured to receive the emitted radiation. A structure is formed on the support, the first LED device, and the second LED device. The structure defines a contoured surface. A material is located adjacently to the contoured surface, wherein the material includes a property adapted to reflect the emitted radiation from the first LED to the second LED. The structure includes an ellipsoid and the contoured surface defines an ellipsoidal surface. First and second foci are defined by the ellipsoid, wherein emitted radiation from the first LED device converges at the first foci and the second foci and is reflected to the second LED device. The device is configured to determine a temperature or a chemical property of an analyte.

19 Claims, 12 Drawing Sheets

(56) References Cited

U.S. PATENT DOCUMENTS

| | | | |
|---|---|---|---|
| 7,557,690 | B2 | 7/2009 | McMahon |
| 7,598,949 | B2 | 10/2009 | Han |
| 7,847,301 | B2 | 12/2010 | Ives et al. |
| 7,897,057 | B1 | 3/2011 | O'Connor et al. |
| 8,714,778 | B2 | 5/2014 | Tang et al. |
| 2006/0043270 | A1* | 3/2006 | Zimmerman ........ A01G 25/167 250/227.25 |
| 2006/0072319 | A1 | 4/2006 | Dziekan et al. |
| 2006/0118807 | A1 | 6/2006 | Ives et al. |
| 2011/0001422 | A1* | 1/2011 | Aanegola, Sr. ..... H01L 25/0753 313/501 |
| 2015/0179827 | A1 | 6/2015 | Rudmann et al. |
| 2016/0018065 | A1* | 1/2016 | Schinagl ............ H01L 25/0753 362/608 |
| 2018/0245753 | A1* | 8/2018 | Magno ..................... F21S 4/20 |

OTHER PUBLICATIONS

V. Lange, F., Lima, D. Kuhlke; Department of Computer and Electrical Engineering, Houchschule Furtwange University, Germany; Sensors and Actuators A 169 (2011) 43-48; Physical: "Multicolour LED in luminescence sensing application", 6 pages; Journal homepage: www.elsevier.com/locate/sna.

Radovan Stojanovic and Dejan Karadaglic; Sensors 2013, 13, 574-586; doi:10.3390/S130100574; sensors issn 1424-8220; www.mdpi.com/journals/sensors; "Design of an Oximeter Based on LED-LED Configuration and FPGA Technology"; 13 pages.

Patent Cooperation Treaty International Search Report and Written Opinion dated Aug. 31, 2018 cited in counterpart PCT/US18/35412 (8 pages).

* cited by examiner

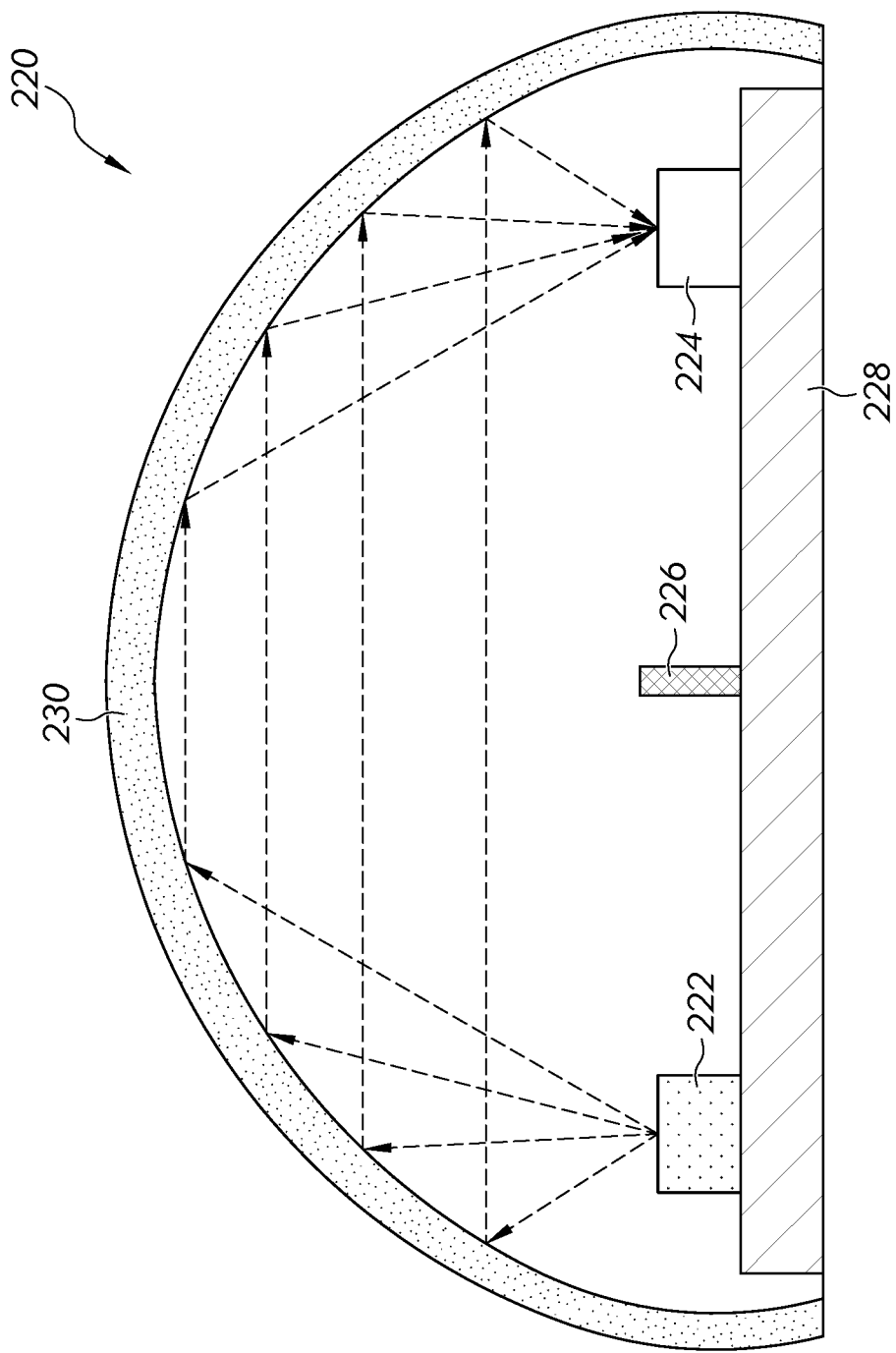

LIGHT EMITTING DIODE SENSOR DEVICE INCLUDING A CONTOURED STRUCTURE

FIELD OF THE INVENTION

The present invention generally relates to light emitting diode (LED) devices, and more particularly to an LED sensor device adapted to determine the properties of an analyte.

BACKGROUND

An LED device is a semiconductor device that includes an interface, or junction, between two types of semiconductor material, one being a p-type semiconductor and the other being an n-type semiconductor. The LED is a special type of diode that emits light. When biased in one direction, a current flows through the device, but when biased in an opposite direction, current does not flow unless in a reverse saturation current mode.

With an appropriate voltage applied across two leads of the device, a light (radiation) is produced which includes a color corresponding to the type of material used to make the semiconducting material of the LED. The LED device has applications in many industries and many types of devices. Since the LED is widely used, the cost of LED devices is generally very low and cost effective. Consequently, the LED device can be found in many different types of electrical products and devices due its ability perform as a low-cost switch or low-cost source of light. Furthermore, it is known in the art, though less well appreciated, that LEDs can absorb radiation to produce an electrical signal though they are seldom used for this application.

It is known in the art that LEDs are relatively selective in both an emission spectrum of light at a particular wavelength, and an absorption spectrum or reception of light of a particular wavelength. LEDs typically absorb radiation with a spectrum that is higher energy and smaller wavelength than the spectrum at which the light is emitted.

Because LEDs also detect light, there are various mechanisms for determining the content of optical signals incident upon an LED junction. For instance, it is possible to measure the light levels incident upon an LED while it is emitting light by measuring the difference it creates in junction impedance. For an LED junction which is not emitting light, it is possible to measure a current which flows with the diode in an under reversed biased condition. For instance it is possible to measure this current directly (e.g. with a picoammeter). Another mechanism for measuring incident light flux is to directly measure the photovoltage generated by illumination. Another mechanism for measuring incident light flux integrated over time is to apply a known reverse bias across the junction (as a capacitive stored charge) and then measure the decay of this voltage value over time. This last mechanism provides a mechanism for simplifying the electronics needed and reducing noise by providing an intrinsically time-integrated data output.

LED behavior can also depend upon the junction temperature of the device. In some embodiments, temperature can be monitored to enable dynamic referencing and calibration for the device. As is known in the art, the temperature measurement and/or control of an LED may be accomplished in a variety of ways.

Even though LED operating characteristics and behaviors are known, LEDs are inefficient absorbers and therefore are generally not used as such for the determination of the characteristics of a physical environment including chemical and physical environments. Consequently, there is a significant need for the unique LED devices, methods, systems and techniques disclosed herein. In addition, there is a significant need for the unique apparatuses, methods, systems and techniques disclosed herein.

SUMMARY

Exemplary embodiments include unique systems, methods, techniques and apparatuses for systems to detect physical and chemical characteristics of the environment to which it is exposed. Further embodiments, forms, objects, features, advantages, aspects and benefits of the disclosure shall become apparent from the following description and drawings.

In the present disclosure, a single LED package including one or more LEDs serves as both a light emitter and a light receiver for performing chemical, physical, and/or environmental detection and thereby reduces or eliminates the need for additional optics, such as lenses, and the associated costs that result. In one embodiment, the LED package is placed in an immediate proximity to a material system which acts to return light back in to the LED package and which alters the sensed characteristics of the returned light (e.g. intensity, wavelength, etc.) in response to environmental stimuli or an analyte (e.g. concentration of a chemical, pH, temperature, etc.). In one or more embodiments, a single LED packages encases multiple LED junctions. In some embodiments, this plurality of junctions includes a set of junctions that interact with light having different spectral characteristics. In some embodiments, this plurality of junctions includes a set of junctions, all of which interact with light with substantially the same spectral characteristics.

In one embodiment, there is provided an LED sensor including a first LED junction configured to emit a radiation and a second LED junction configured to receive a radiation. A package encapsulates the first LED junction and the second LED junction, wherein the package defines a contoured envelope. A material is located adjacently to the contoured envelope, wherein the material includes a property adapted to reflect the emitted radiation to the second LED. In another embodiment, the contoured envelope is configured to absorb and to re-emit light to the second LED when the envelope includes phosphorescent/fluorescent materials.

In another embodiment, there is provided an LED sensor including a support and a first LED device disposed on the support. The first LED device includes a single LED junction configured to emit a radiation. A second LED device is disposed on the support and includes a single LED junction configured to receive a radiation. A structure is formed on the support, the first LED device, and the second LED device, wherein the structure defines a contoured surface. A material is located adjacently to the contoured surface, wherein the material includes a property adapted to reflect the emitted radiation from the first LED to the second LED.

BRIEF DESCRIPTION OF THE DRAWINGS

FIG. 17 is a schematic view of an LED sensor having a first LED, a second LED, and a barrier disposed between the first LED and the second LED.

DETAILED DESCRIPTION OF ILLUSTRATIVE EMBODIMENTS

Figure 1A:
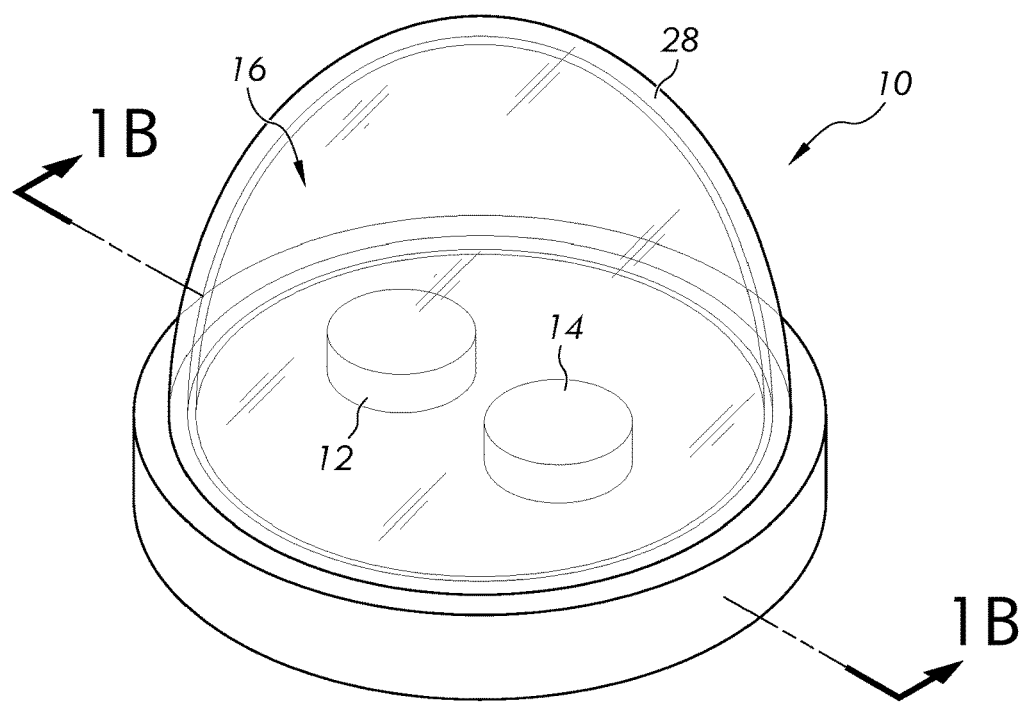
FIGS. 1A and 1B illustrate an LED sensor having a first LED and a second LED enclosed in a contoured structure.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1B:
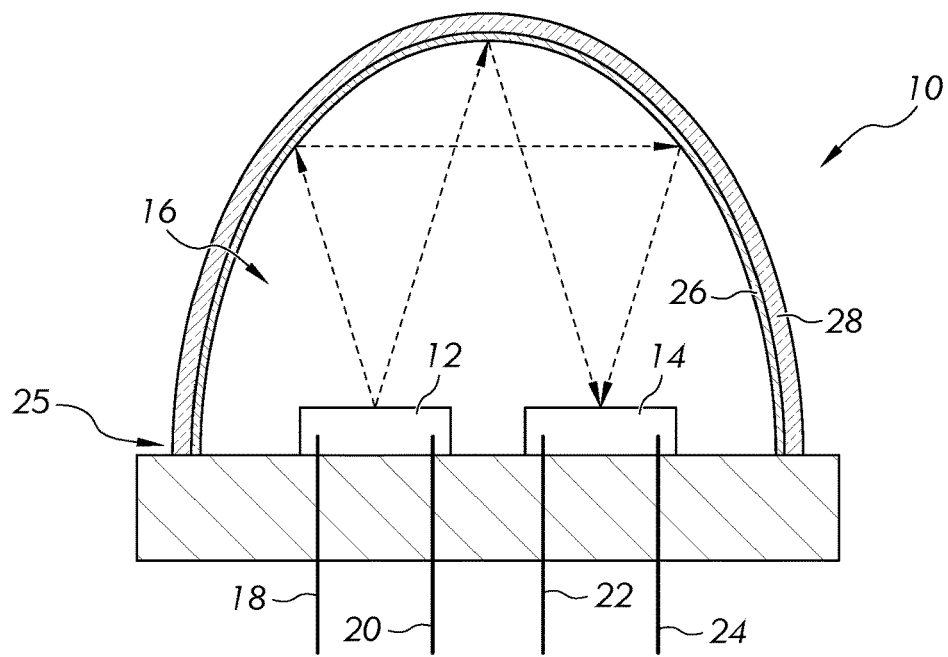

FIGS. 1A and 1B illustrate a schematic view of an LED sensor 10 having a first LED 12 and a second LED 14 enclosed in a contoured structure 16. Each of the LEDs includes a single LED junction of the same color encased within the single contoured structure 16, which in this embodiment is a single or unitary package formed of a resinous material, such as polyurethane or epoxy. The LED 12 includes an anode 18 and a cathode 20. LED 14 also includes an anode 22 and a cathode 24, as is understood by those skilled in the art. Light emitted from LED 12 is internally reflected and absorbed at the junction of LED 14, where the absorbed light provides a detectable electronic response. A material layer 25, formed of one or more types of materials, alters the illumination levels impinging upon the sensing junction of LED 14. In remaining figures, the electrical leads to the device are not shown.

In the embodiment of FIG. 1, the material layer 25 includes a reflective layer 26, or encasing layer, that modulates the reflectivity of the emitted light radiation generated by the LED 12 within the structure 16, in response to the environmental chemical potential of an analyte. The material layer 25 further includes an optical absorber layer 28, adjacently located to the reflective layer 26, which absorbs emitted light and prevents stray light from entering into the LED sensor 10. In one exemplary embodiment, each of the first and second LEDs 12 and 14 are green LEDs (565 nm) encased inside of the structure 16 which is coated with a thin layer of palladium (Pd) alloy (or a stack including palladium alloy and additional metal layers which change optical reflectivity due to hydrogen absorption) as the reflective layer 26. In this embodiment, the LED sensor 10 is configured to detect the presence of hydrogen gas ($H_2$). In other embodiments, the structure 16 is configured to detect analytes other than hydrogen. Such analytes include, but are not limited to, oxygen and volatile organic compounds (VOCs). In these embodiments, the structure 16 includes one or more different reflective layers and/or different geometric architectures. Additionally, the described embodiments are not limited to detection of a gas, but also are configured to detect a chemical species.

Figure 2:
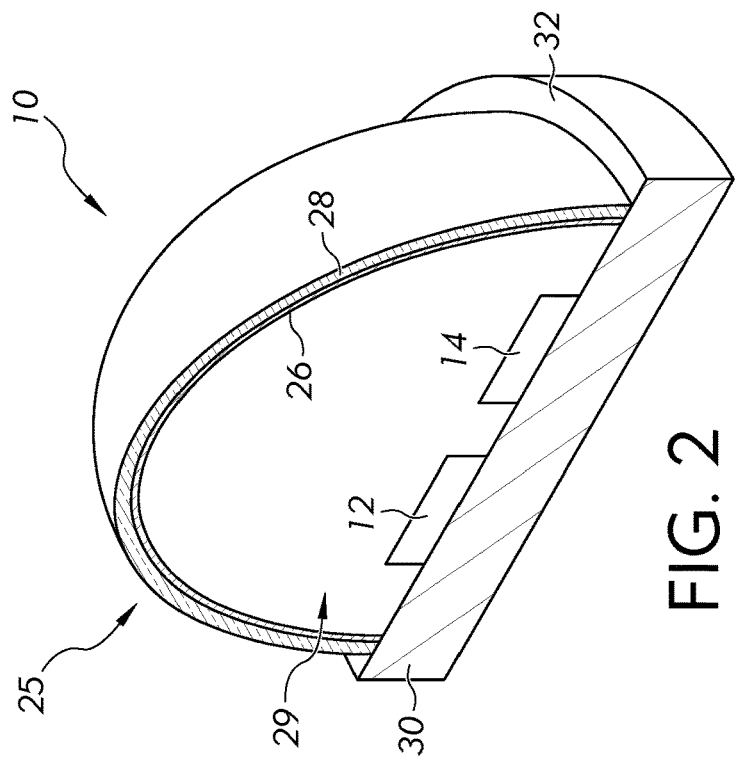
FIG. 2 is a solid sectional perspective view of an LED sensor having two LEDs enclosed in a contoured structure sectioned along a centerline thereof.

FIG. 2 illustrates a solid sectional perspective view of the LED sensor 10 of FIG. 1 having the two LEDs 12 and 14 enclosed in a contoured structure 29, sectioned along a centerline thereof. As can be seen in FIG. 2, the contoured structure 29 is configured to include a base 30 which extends laterally from the material layer 25. As used herein, a contoured structure includes, but is not limited to, structures having spherical shapes, ellipsoidal shapes, and flat rectangular shapes. A surface 32 of the base 30 provides an interface between terminating edges of each of the materials 26 and 28 to provide the consistently formed material layer 25. Since the material layer 25 provides both reflection and absorption, the interface at the surface 32 is consistently controlled to prevent misdirected internal reflection as well as to prevent stray light from entering the structure 29. In other embodiments, the base 30 is not included, and the LEDs extend from a different supporting structure, including the terminals, the anode 18 and the cathode 20.

Figure 3:
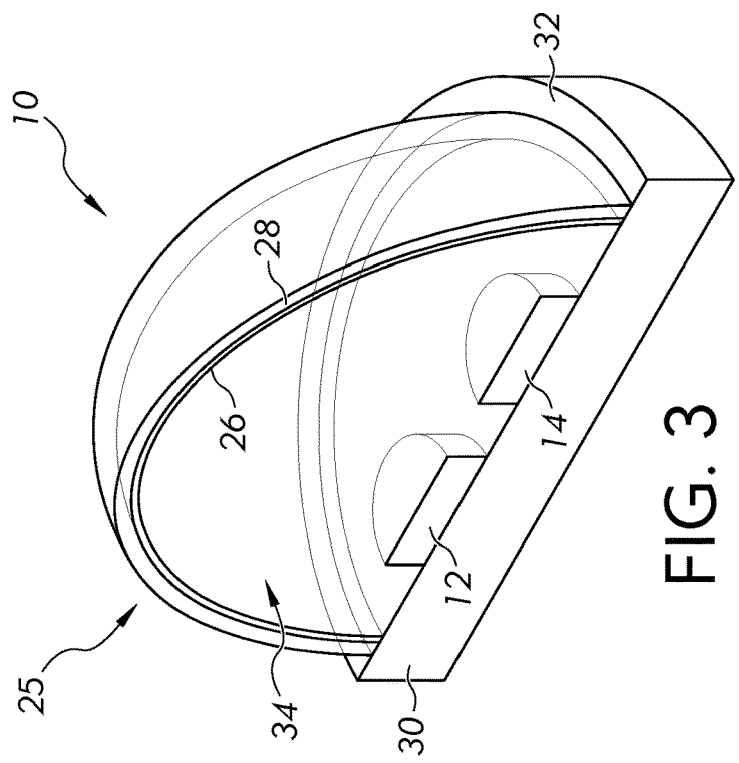
FIG. 3 is a sectional perspective view of an LED sensor having two LEDs enclosed in a transparent contoured structure sectioned along a centerline thereof.

FIG. 3 is a sectional perspective view of the LED sensor 10 having two LEDs 12 and 14 enclosed in a transparent contoured structure 34 sectioned along a centerline thereof. In other embodiments, the contoured structure is not completely transparent, but is semi-transparent or translucent. Such embodiments include materials which modulate the spectral transparency characteristics of the contoured structure and include materials such as a dye. Consequently, the performance of the LED sensors, in one or more embodiments, is controlled or adjusted by selecting the types of LEDs, the type of material used to form the contoured structure, and the types of material used to form the material layer 25, including the reflective layer 26 and the optical absorber layer 28. The LEDs are of different sizes and shapes and a circular configuration is one example. Other shapes of LEDs are also contemplated including rectangular, square, and hexagonal LEDs. In these and other embodiments, one of the LEDs functions as an emitter and another LED functions as a photodiode. In different embodiments, a photodiode is used in place of the LED to receive the light transmitted by one or more LEDs.

Additionally, the thickness of each of the layers 26 and 28, in different embodiments, is determined based on the desired function of the sensor. For instance, each of the layers 26 and 28, in different embodiments, includes the same thickness. In FIGS. 2 and 3, the layers are of a different thickness.

The structure 16 of the LED sensor 10 is coated or encapsulated with a material that is optically responsive to a particular environmental condition which is desirable to test. In other embodiments, the structure 16 is embedded with the desired material. Such material systems include, but are not limited to: i) reflective and/or partially reflective films which alter reflective properties (e.g. efficiency, spectrum, specularity/diffuseness, etc.) upon exposure to environmental stimuli; and ii) fluorescent and/or phosphorescent films which alter returned light characteristics (e.g. yield, spectrum, time constant, etc. for emission). In other embodiments, color change dyes are fixed into the material layer 25, which is configured as a permeable layer (e.g. a polymer layer, a gel, etc.). For instance, a halochromic dye, a thermochromic dye, or other dyes, are fixed in a gel which is placed in proximity to the LED structure 16. In such embodiments, incorporation of the dye into a larger body allows light to travel through the gel and then reflects the light back to the LED, as will be further described below.

In some embodiments, additional optical material is incorporated, in addition to, or instead of, the environmentally sensitive optical material to enhance the signal characteristics of the overall device. For instance, an optically absorbing film is used over the top of an environmentally responsive optically reflecting film to reduce secondary light reflections. In another configuration, an optically reflective film is used over the top of a fluorescent and/or phosphorescent film to maximally return an optical signal back in to the receiving LED for detection. In still another embodiment, an optically reflective film is used over the top of a layer containing chromic sensing materials (e.g. halochromic, ionochromic, solvatochromic, etc.) so that the reflective film returns light to the receiving LED and the chromic layer modulates the sensible characteristics (e.g. intensity, spectrum, etc.). In these and other embodiments, overcoating films are constructed to enable permeation of analytes through the overcoating film to the sensing layer. In some embodiments, both functions or absorption and reflection are incorporated into a single layer—for instance a chromic material is incorporated into an analyte permeable material layer (e.g. a polymer) which is configured to be reflective (e.g. as a dielectric wavelength-matching reflective coating).

Figure 4:
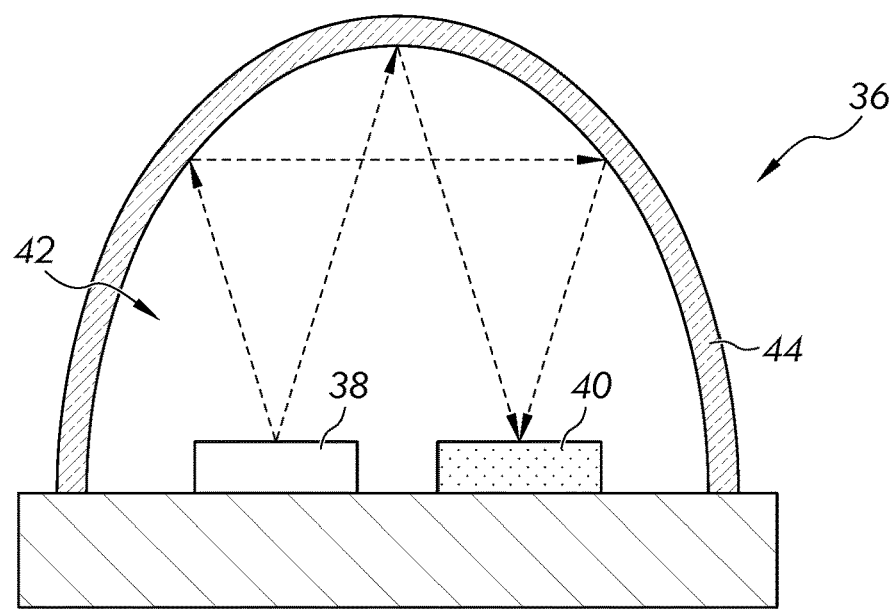
FIG. 4 is a schematic view of an LED sensor having a first LED and a second LED enclosed in a contoured structure.

FIG. 4 is a schematic view of an LED sensor 36 having a first LED 38 and a second LED 40 enclosed in a contoured structure 42. A material layer 44 having a single layer of material is located on the contoured surface of the structure 42. In this embodiment, the LED junction of LED 38 is of a different color than the LED junction of LED 40. Both LEDs 38 and 40 are encased within the single structure or packaging 42. Light emitted from LED 38 is internally reflected and absorbed by the junction of the second LED 40, where it creates a detectable electronic response. The material layer 44 encases the exterior surface of the structure 42 to modulate reflectivity of the light transmitted from LED 38 in response to an external environmental stimulus. The material layer 44 alters the illumination levels impinging upon the junction of the sensing LED 40 junction. In one embodiment, the emitting LED 38 is green LED emitting around 565 nm, and the absorbing LED 40 is a yellow emitting LED configured to receive relatively efficiently at around 565 nm. The material layer 44 is a thin layer of Pd to detect the presence of H2. In this and other embodiments, the contoured surface of the structure and the material layer are configured to provide an optically sculpted reflector. By selecting the shape of the contoured surface and the type of material, the optically sculpted reflector provides for a predetermined light path or paths within the sensor to optimize the transmission and reception of light by the LEDs.

Figure 5:
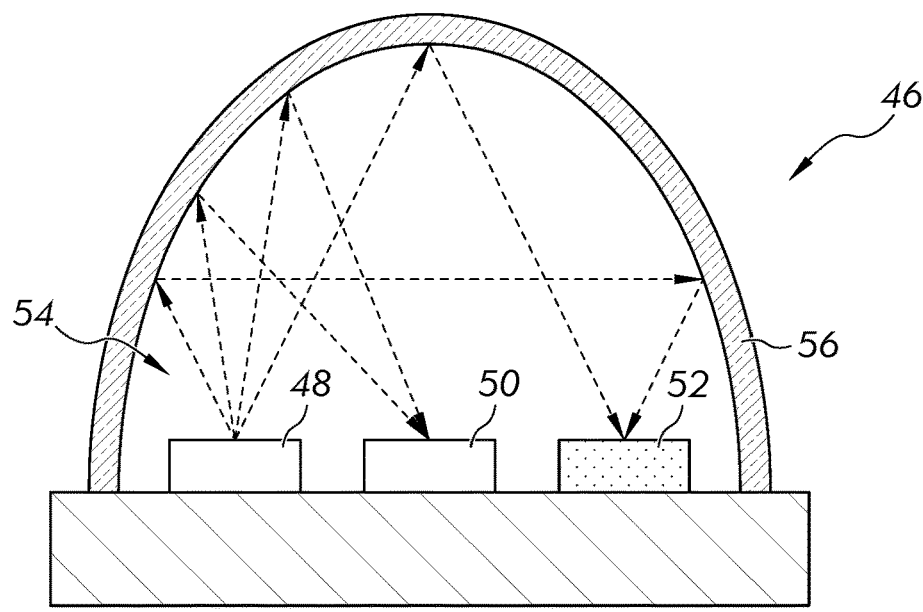
FIG. 5 is a schematic view of an LED sensor having a first LED, a second LED, and a third LED enclosed in a contoured structure.

FIG. 5 is a schematic view of an LED sensor 46 having a first LED 48, a second LED 50, and a third LED 52 enclosed in a contoured structure 54. In this embodiment, the junctions of the three LEDs include two different colors encased within a single packaging. Light emitted from LED 48 is internally reflected and absorbed by the LED 50 and LED 52, where the absorbed light provides a detectable electronic response. A material layer 56 encases the structure 54 and modulates reflectivity in response to an environmental stimulus and thereby alters the illumination levels impinging upon the sensing LED junctions of LEDs 50 and 52. In one embodiment, the LED 48 is an emitting green LED, having an emission peak of approximately 565 nm, and the LED 50 is an absorbing LED having an absorbing green emission peak of approximately 565 nm. The LED 52 is an absorbing LED having a yellow emission peak of approximately 585 nm. The structure 54 is coated with material layer 56 which includes single thin layer of Pd to detect the presence of H2. In different embodiments, the range of thickness of the material layer, (a "thin layer"), is approximately between 5 nanometers (nm) and 250 nm and more commonly between approximately 25 nm and 150 nm. For a majority of metal based reflective stacked layers, the thickness does not drop below a few nanometers nor does the thickness exceed a few hundred nanometers.

Figure 6:
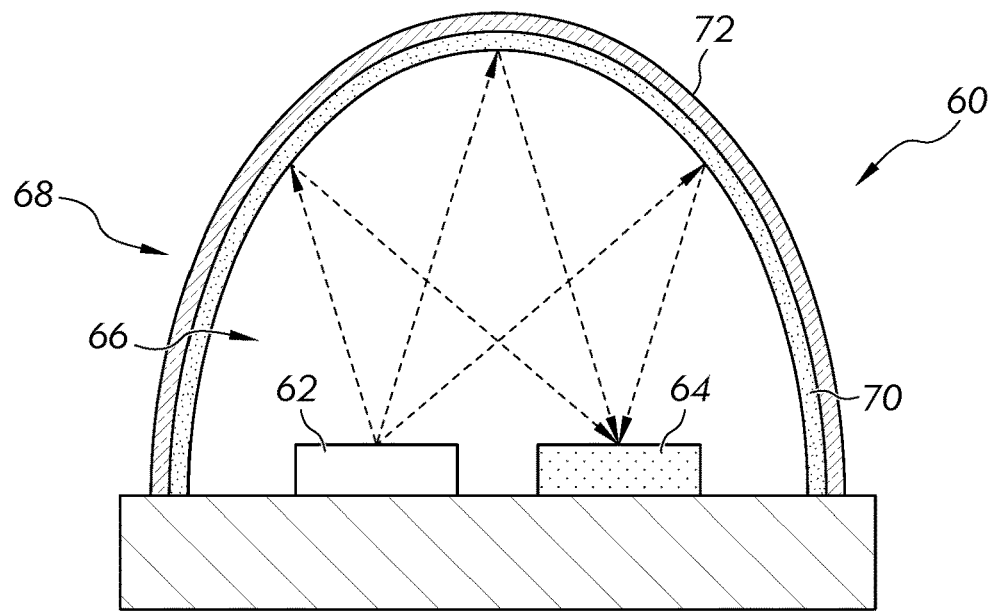
FIG. 6 is a schematic view of an LED sensor having a first LED and a second LED enclosed in a contoured structure.

FIG. 6 is a schematic view of an LED sensor 60 having a first LED 62 and a second LED 64 enclosed in a contoured structure 66. In this embodiment, the LED junctions of each of the LEDs 62 and 64 are of differing colors encased within a single packaging of the contoured structure 66. Light emitted from the LED 62 is absorbed and re-emitted by material layer 68 located at the surface of the LED structure 66. The re-emitted light is absorbed by the second LED junction of the LED 64 where the absorbed re-emitted light creates a detectable electronic response. The material layer 68 includes a first layer 70 which provides environmentally modulated photoluminescence in response to an external environmental stimulus and thereby alters the illumination levels impinging upon the sensing LED junction of LED 64. A reflective layer 72 disposed adjacently to the photoluminescent layer 70 enhances the amount of light returned for sensing by the LED 64. In one embodiment, the layer 72 is adapted to reflect external radiation and to prevent at least a portion of the external radiation from being received by the LED 64. In another embodiment, the layer 72 is adapted to absorb external radiation to prevent interference with the measurement of an analyte.

In one embodiment, the LED 62 includes an emitting blue LED junction having an emission peak of approximately 450 nm. The LED 64 includes an absorbing yellow LED junction having an emission peak of approximately 585 nm. In one embodiment, the LED's absorption spectrum is substantially insensitive to the light spectrum emitted by the blue LED 62. Each of the LEDs 62 and 64, in this embodiment, are encased inside of the structure 66 in which the layer 70 is coated on the surface of the structure 66 as a thin layer of a phosphor which absorbs the blue radiated light and which emits as a yellow radiation wherein this absorption/re-emission process is quenched by external oxygen (O2) to detect the presence of O2.

Figure 7:
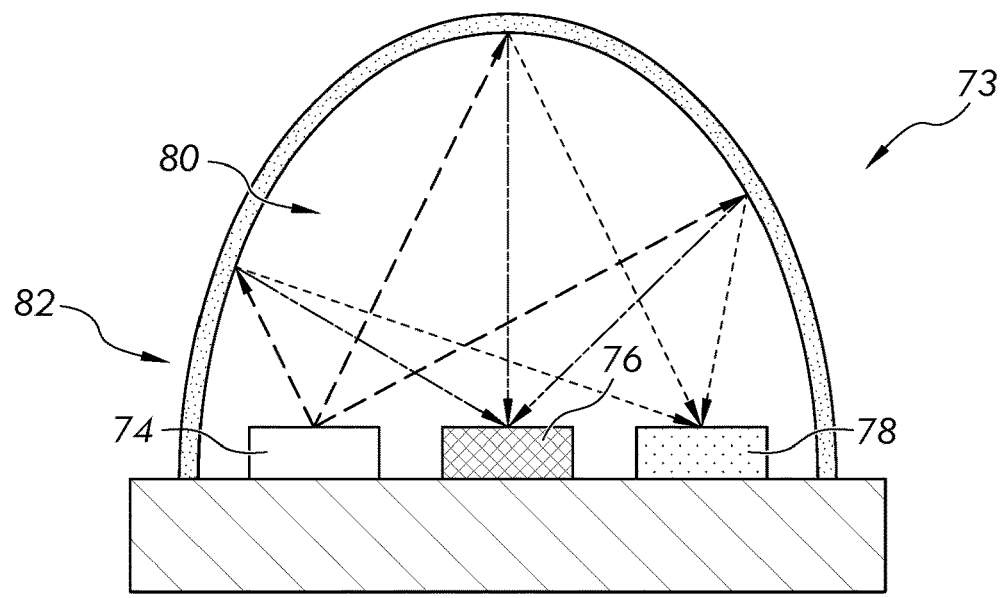
FIG. 7 is a schematic view of an LED sensor having a first LED, a second LED, and a third LED enclosed in a contoured structure.

FIG. 7 is a schematic view of an LED sensor 73 having a first LED 74, a second LED 76, and a third LED 78, each of which is enclosed in a contoured structure 80. Each of the LEDs 74, 76, and 78 include LED junctions of a differing color encased within a single packaging of the structure 80. Light emitted from LED 74 is absorbed and re-emitted by a material 82, which is a single coating layer displaced on the surface of the structure 80. The light emitted from the LED 74 is then absorbed by the other two LED junctions of the second LED 76 and the third LED 78, where the absorbed light provides a detectable electronic response at the junction of each of the two LEDs 76 and 78. In different embodiments, the encasing layer 82 is fluorescent or phosphorescent and it's response to certain analytes modulates the spectrum of light which is re-emitted. This spectrum shift subsequently measured by the two absorber LEDs 76 and 78. In one embodiment, the LED 74 is an emitting violet LED having an emission peak of approximately 425 nm. The LED 76 is an absorbing orange LED having efficient absorption around 610 nm. The LED 78 is an absorbing red LED having efficient absorption around 650 nm and wherein the two LEDs 76 and 78 have substantially differentiated absorption efficiencies in these two spectral regions 610 nm versus 650 nm. The LEDs 74, 76, and 78 are encased inside the structure 80, which is coated with a thin layer 82 of a phosphor which absorbs in the blue and emits a broad lower spectrum which is measured by LEDs 76 and 78 with spectral properties modified by the presence of a suitable analyte which enables the detection of local analyte levels. This may be used to detect various analytes such as oxygen and $Zn^{++}$. In the case of $Zn++$, an encasing layer includes a porphyrin such as the porphyrin designated "P1" by Y. Lv, et al. as described in *A Sensitive Ratiometric Fluorescent Sensor for Zinc(II) with High Selectivity* Sensors 2013, 13(3) 3131-3141. (doi:10.3390/s130303131).

Figure 8:
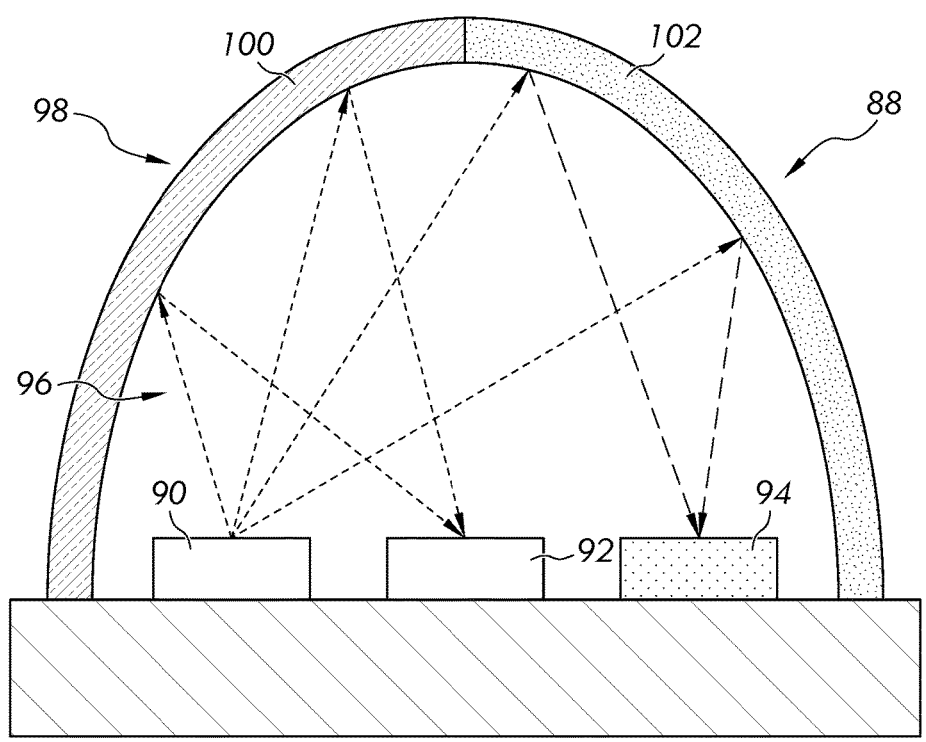
FIG. 8 is a schematic view of an LED sensor having a first LED, a second LED, and a third LED enclosed in a contoured structure.

FIG. 8 is a schematic view of an LED sensor 88 having a first LED 90, a second LED 92, and a third LED 94 enclosed in a contoured structure 96. In this embodiment, the LED junctions of LEDs 90, 92, and 94 are of two differing colors encased within the structure 96 having a single packaging which is coated by a material layer 98, having two different environmentally responsive film layers, a layer 100 and a layer 102. Light is emitted from LED 90 to each of the coating film layers 100 and 102. The reflected light from layer 100 is absorbed and measured by the LED 92, which is efficient for absorbing light of the same color as the light emitted by LED 90. The reflected light from the other film layer 102 is absorbed by the film layer 102 and re-emitted at another frequency. This re-emitted light is then absorbed and measured by the LED 94 having an absorption spectrum matched to the re-emitted spectrum from layer 102.

Figure 9:
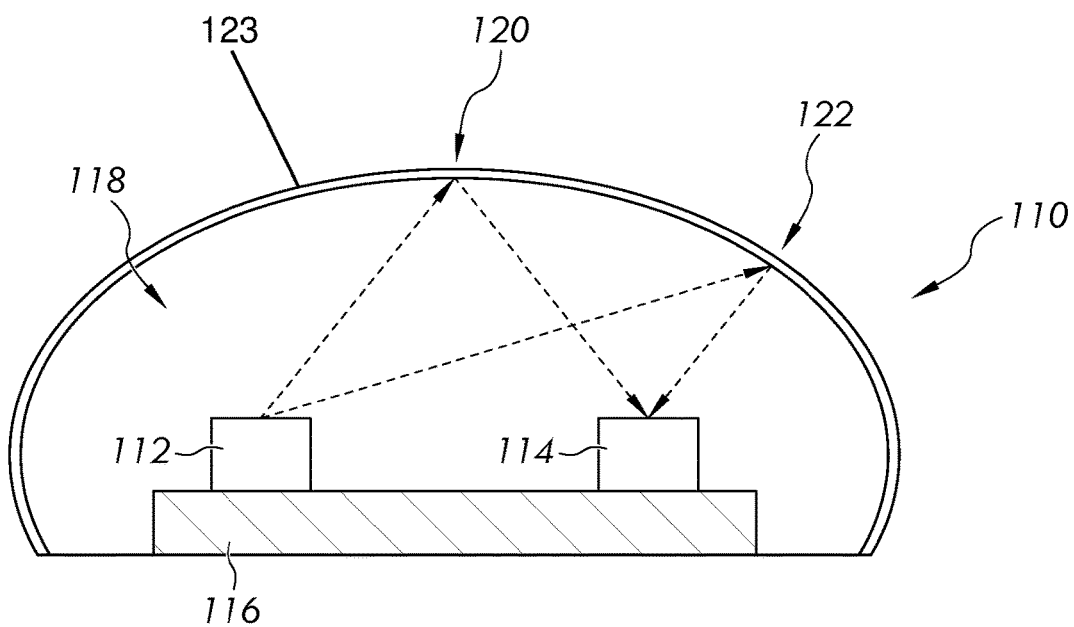
FIG. 9 is a schematic view of an LED sensor having a first LED and a second LED located on a support, all of which are enclosed in a contoured structure.

FIG. 9 is a schematic view of an LED sensor having a first LED 112 and a second LED 114 located on a support 116, all of which are enclosed in a contoured structure 118. The LED 112 and the LED 114 each include a single LED junction of the same color encased within the structure 118 having a single packaging. The support 116 is a single anvil, where the packaging is shaped in the form of a partial-ellipsoid. In some embodiments the form of the partial-ellipsoidal shape is chosen such that the ellipsoid defines two foci and the foci are located at or near the LED junctions which are supported on the support 116. Such ellipsoids are commonly formed as ellipsoids of revolution about the axis of the line which joins the two foci, as illustrated. In other embodiments, ellipsoids having other than two foci are contemplated.

As used herein, foci refers to the two points enclosed in the ellipsoid which possess the characteristic that a ray which leaves one of the foci and is transmitted from one LED, specularly reflected from the ellipsoidal surface, and travels to the other foci located at the other LED. The regions immediately adjacent to each foci is referred to as a "focal region" and specular reflection from the ellipsoidal surface will act to direct most of the light, but not necessarily one hundred percent of the light, which is emitted from one focal region to the other focal region. These focal regions are the spatial regions occupied by LEDs 112 and 114 and the immediate vicinity of LEDs 112 and 114. The focal regions do not lie on the surface of the ellipsoids, but are instead located on or near the LEDs 112 and 114 such that the illustrated rays are illustrative of many rays which are emitted from LED 112 and then reflected from the surface of the ellipsoid and back to LED 114.

The various embodiments, therefore, include a structure configured to increase the amount of applied incident light directed to a receiver LED. These configurations not only increase the amount of a photovoltage signal generated by the receiver LED, but also reduce the amplitude of the noise present in the signal being measured. Thus, the use of higher lighting levels is advantageous and improves the signal quality provided by the LED sensor. Furthermore, the use of such focusing structures, such as an ellipsoid, which concentrates the amount of light delivered to a receiver LED, is advantageous to enhance the signal to noise ratio of the delivered signal.

Each of LEDs 112 and 114 are placed at one of the focal regions of the ellipsoid. Light emitted from the LED 112 is internally reflected and absorbed by the junction of LED 114, which is placed at the other focal region of the ellipse, where this reflected light creates a detectable electronic response. The ellipsoidal geometry of the packaging maximizes the light delivered to the second LED 114 from the first LED 112. The structure 118 includes a material layer 123. The material layer 123 encases the structure 118 and modulates reflectivity in response to an environmental stimulus and thereby alters the illumination levels impinging upon the sensing LED 114. The structure 118 includes an ellipsoid and the contoured surface defines an ellipsoidal surface. First and second foci are defined by the ellipsoidal surface.

Figure 10:
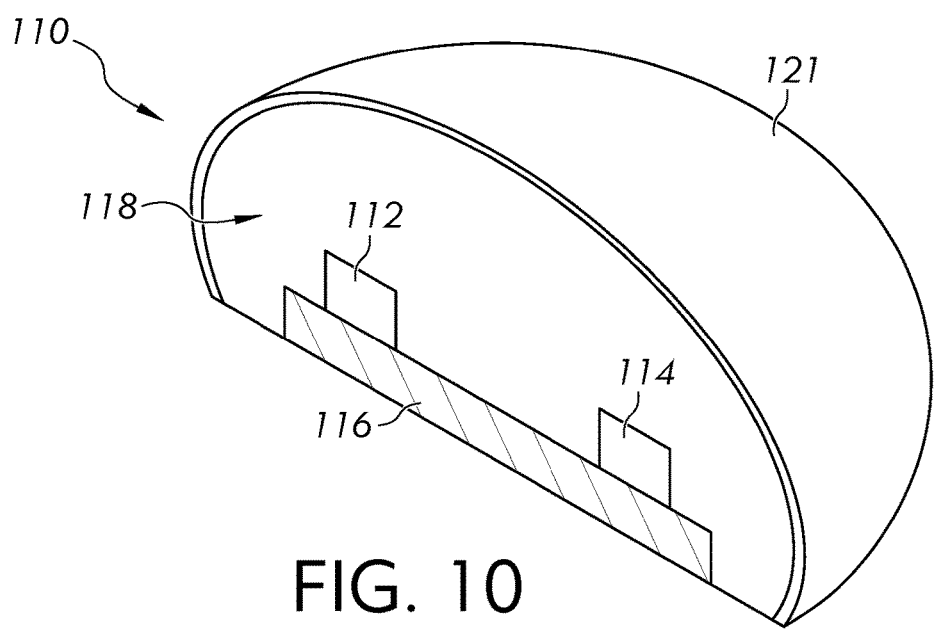
FIG. 10 illustrates a solid sectional perspective view of an LED sensor having two LEDs enclosed in an elliptically contoured structure sectioned along a centerline thereof.

FIG. 10 illustrates a solid sectional perspective view of the LED sensor 110 having two LEDs enclosed in the ellipsoidally contoured structure sectioned along a centerline thereof. In this embodiment, the exterior surface of structure 118 is covered by a material layer 121. The material layer 120, in different embodiments, includes one or more layers as described in this disclosure. The exterior surface of the surface structure 118 is configured to define the ellipsoidal shape to achieve the desired focal regions of the ellipsoid. The ellipsoidal contour configuration is most effective for boosting efficiency for reflective layers that are specular or near specular in their reflectance properties. The LEDs are placed appropriately on the support 116 to transmit and receive the LED light.

Figure 11:
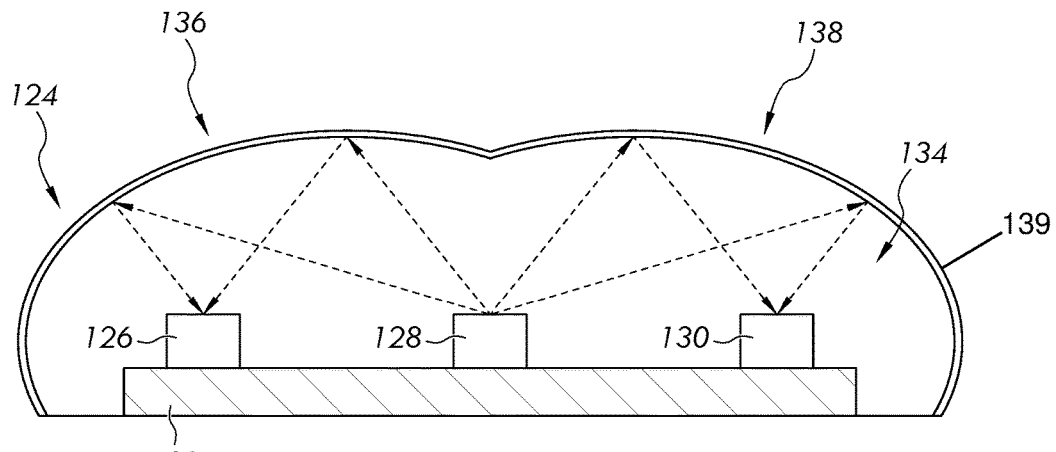
FIG. 11 is a schematic view of an LED sensor having three LEDs enclosed in an elliptically contoured structure having two semi-ellipsoids.

FIG. 11 illustrates a schematic view of an LED sensor 124 having a first LED 126, a second LED 128, and a third LED 130, each of which is disposed on a support 132. The LEDs and the support 132 are enclosed in a contoured structure 134, which is contoured to include the union of two intersecting semi-ellipsoids to form a compound ellipsoid. Each of the first, second, and third LEDs 126, 128, and 130 include an LED junction of the same color encased within the contoured structure 134, which is a single unitary packaging. The support 132 is a single anvil. The structure 134 is shaped in the form of a first semi-ellipsoid 136 intersecting with a second semi-ellipsoid 138. Each LED is located at a focus focal region on the anvil 132 to transmit or to receive light directed to or reflected by one or more of the semi-ellipsoids. Light emitted from LED 126 is internally reflected and absorbed by the other LED junctions of LEDs 128 and 130, where a detectable electronic response is generated by the LED. The ellipsoidal geometry of the packaging maximizes the amount of light delivered to the LED junctions of LEDs 128 and 130 received from the first LED junction of LED 126. The structure 134 includes a material layer. The material layer 139 encases the structure 134 and modulates reflectivity in response to an environmental stimulus and thereby alters the illumination levels impinging upon the sensing LED junctions of the LEDs 126 and 130. In other embodiments, the layer 139 is composed of multiple geometric regions with a differentiated functional characteristic (e.g. some being sensitive to the environment and others not being sensitive). In still other embodiments, the layer 139 is composed of differentially sensitive environmental components configured provide interference mitigations. In structures having differentially sensitive components to form sensor arrays, detection of multiple analytes and/or mitigation of interference effects from other environmental components is provided.

While FIG. 11 illustrates one embodiment of an LED sensor formed of two intersecting ellipsoids, in other embodiments, an LED sensor is contemplated to include more than two intersecting ellipsoids. In these embodiments, the number of LEDS is determined based on a desired result and can include one or more LEDs.

In other embodiments, multiple intersecting ellipsoids share a single focal point at the intersection. One such embodiment includes a "flower" geometry where multiple ellipsoids intersect to provide a single focal point. In another embodiment, a "chained" geometry includes multiple ellipsoids which intersect in a geometric sequence. For examples, one "chained" geometry includes three ellipsoids A, B, and C and three focal points 1, 2, 3, with focal point 1 being shared by ellipsoid A and C, focal point 2 being shared by A and B, and focal point 3 being shared by B and C.

Figure 12:
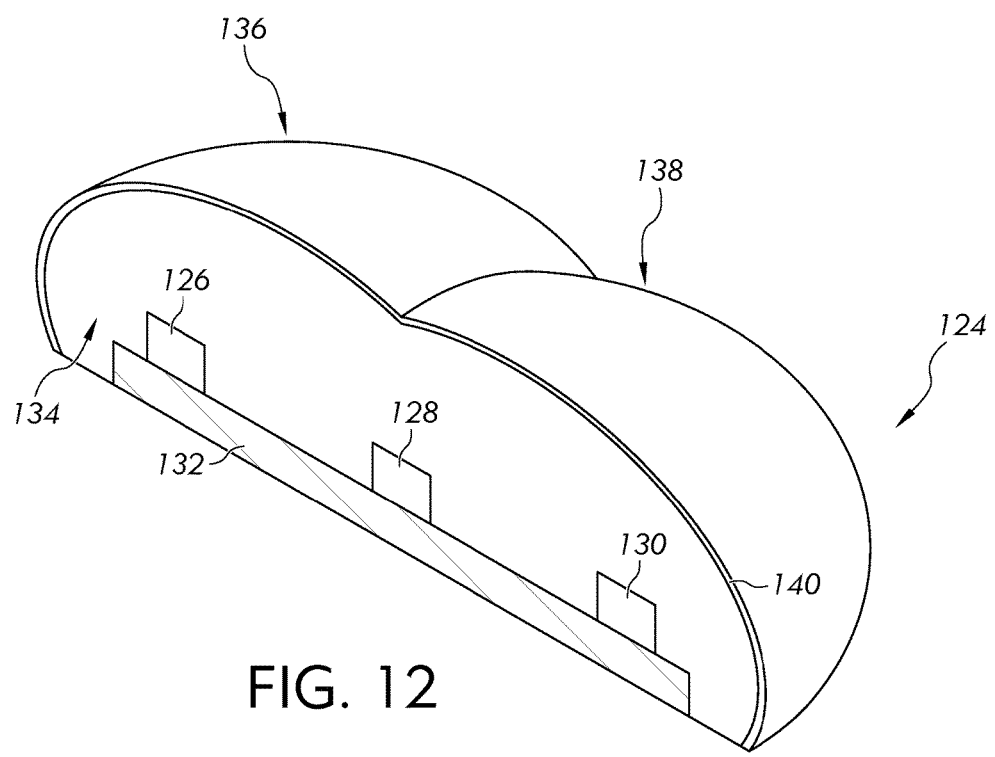
FIG. 12 is a sold sectional perspective view an LED sensor having three LEDs enclosed in an elliptically contoured structure having two semi-ellipsoids.

FIG. 12 is a solid sectional perspective view the LED sensor having the three LEDs 126, 128, and 130 enclosed in an elliptically contoured structure having the semi-ellipsoid 136 and the semi-ellipsoid 138. In this embodiment, the exterior surface of structure 134 is covered by a material layer 140. The material layer 140, in different embodiments, includes one or more layers as described in this disclosure. In other embodiments, the material layer 140 on the semi-ellipsoidal portion 136 is different than the material on the semi-ellipsoidal portion 138. In this embodiment, one of the LEDs 126 and 128 enables one of the device couples to serve as an internal reference and the other of the LEDs 128 and 130 serve as a sensor. That is, light emitted from the center LED is focused onto both of the two absorber LEDs, 126 and 130 by the geometry of the compound ellipsoid. By using films which have differentiated responses to the local environment in their reflectivity the comparison of the two output signals from 126 and 128 can provide information to compensate against non-measurement effects (e.g. reduced emitter efficiency, electronic noise, etc.) By this configuration, the sensor enables referencing of the device over its lifetime.

In one or more embodiments, the LED packaging structure is constructed to maximize the amount of environmentally signaling light that the system returns to the absorbing LED. For instance, in systems using a variable reflectance film coated onto the top of the structure encapsulating the LEDs, the structure is constructed into an ellipsoidal or partially ellipsoidal morphology as described with respect to FIGS. 9-12. In these types of structures, the absorber and emitter LEDs are placed substantially at the focal region for the ellipsoid to maximize the amount of light which is directed from the emitter to the receiver. Since the light emitted from the LEDs includes some spatial extent or expanse, as opposed to being true point emitters, the geometry of the structure should be chosen to enable maximized receipt of light from the receiver LED and minimal return of light to the emitter LED. In general, this will be accomplished by the placement of the LEDs to be optimally placed essentially at the foci, and in some preferred embodiments for the receiver LED to be larger in area than the emitter LED, and in some embodiments for the area near the receiver LED to be coated in a light absorbing coating to prevent light which does not impinge upon the receiving LED to be scattered. This enables maximization of light to travel from the emitter LED to the material layer and then to reflect and travel back to the absorber LED to provide maximization of the signal generated by this architecture. Furthermore, in other embodiments, similar structures such as unions of intersecting ellipsoids are provided to create architectures to focus the light emitted from a point-like source to be focused onto multiple point-like sensor elements. Also, for embodiments in which sensing is carried out by an optical conversion process which does not maintain specularity for the light produced (e.g. fluorescence), the packaging structure may be shaped to optimize the delivery of output light onto the modulating layer (e.g. fluorescent layer) and then deliver the resulting signal light onto an opto-electronic sensing element.

Figure 13:
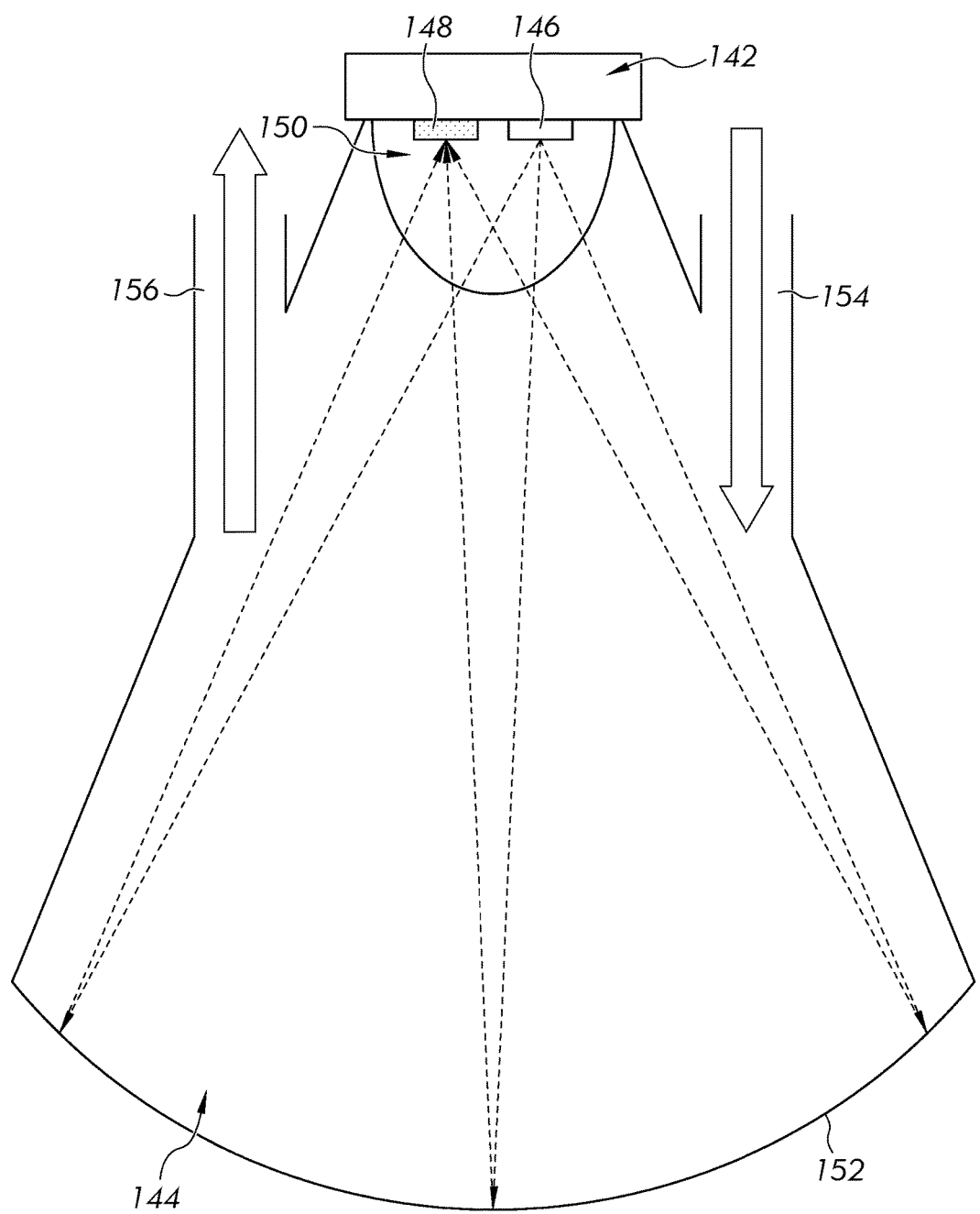
FIG. 13 is a schematic view of an LED sensor disposed in an analyte sensing conic-section-spheric chamber.

FIG. 13 is a schematic view of an LED sensor 142 disposed in an analyte sensing conic-section-spheric chamber 144. The LED sensor 142 includes a first LED 146 and a second LED 148. The LED 146 is used as an emitter LED and the LED 148 is used as a receiver LED. The LED junctions of each of the LEDs 146 and 148 are of differing colors encased within a single packaging structure 150. Light is emitted from the LED 146 out of the structure 150 into an analyte sensing conic-section or partial-spheric chamber 144 and is reflected from a retroreflective surface 152 and returned to the LED sensor 142, where the reflected light is absorbed and detected by the LED 148. Analytes are introduced to and extracted from the chamber 144 through a first port 154 and a second port 156. This enables the sensor 142 to measure the analyte via optical absorption. The single packaging, chamber geometry and retroreflective surface design enables the system to provide improved robustness with respect to small changes in alignment of the sensor 142 with the chamber 144. It is notable that this provides a simplified system for enabling reduced complexity and cost for alignment needs for the overall device.

In this and other embodiments, one or more of the LEDs includes an encasing layer which provides an optical conversion layer (e.g. fluorescent, phosphorescent) incorporated in immediate proximity to the LED to provide the optimized geometric characteristics for the point-like light-source and receiver geometry. The encasing layer provides an optical output of a particular wavelength for sensing by another LED. The encasing layer, however, acts a filter such that light reflected back to the LED source is not of a suitable wavelength to be absorbed by the emitter LED which tends to mitigate potential interference (e.g. due to LED light source output instabilities) caused by reflected light back into the emitting LED.

Figure 14:
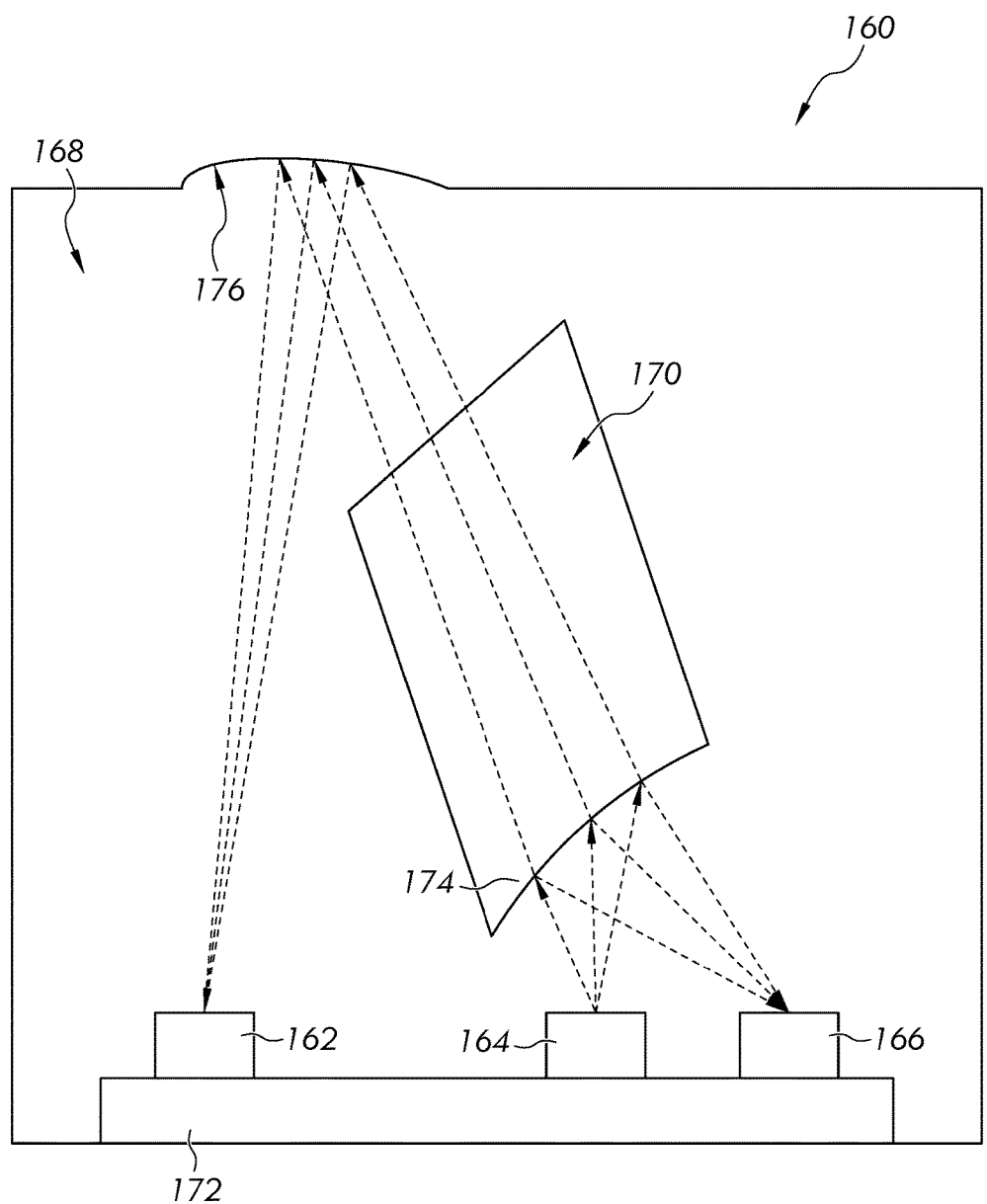
FIG. 14 is a schematic view of an LED sensor having a first LED, a second LED, and a third LED enclosed in a structure having a void space.

FIG. 14 illustrates a schematic view of an LED sensor 160 having a first LED 162, a second LED 164, and a third LED 166 enclosed in a structure 168 having a void space 170. Each of the three LEDs 162, 164, and 166 include LED junctions which are supported on a common anvil 172. The LEDs 162, 164, and 166 include two colors, such that LED 164 is selected to emit some color and the remaining two LEDs 162 & 166 are of a color which is selected to absorb some portion of the spectrum emitted by 164. The LEDs are encased within the structure 168 which includes a single package, wherein the package includes a void space 170, also called a cell, into which an analyte penetrates for sensing. This void cell, in one embodiment, will be formed as a hole into or tunnel through the package which allows analyte to flow into and out of said void cell. Light is emitted from the LED 164 and is substantially transmitted to a surface 174 of the void space 170. The surface 174 is located at an interface between the void space 170 and the material comprising the structure 168. The surface 174 is shaped to focus interfacially reflected light onto one of the sensor LEDs, LED 166. The remaining light is transmitted through the void space cell and onto an area 176 located at an interior surface the packaging structure 168. The area 176 is shaped as a focusing feature or form which focuses the received light and reflects or transmits this focused light onto the LED 162. In one or more embodiments, the surface of the package and in particular, area 176, is treated or coated to enhance the reflection of light form the surface, for instance by silvering. This enables sensing or detection of analytes within the void space and provides device referencing using light reflected to LED 166. For the purposes of referencing, light received by LED 166 is insensitive to the environment whereas the light received by LED 162 is modulated by the environment to insure that the sensor dynamically compensates for changing operating characteristics, such a drift, over a lifetime of the device. The packaging structure is constructed into a form which contains the void space into which analyte readily penetrates for detection. In one embodiment, such constructions includes a geometry in which light is emitted from one LED, traverses the void space, and then encounter a surface of the packaging structure which acts to reflect and focus the light onto a sensing LED.

Figure 15:
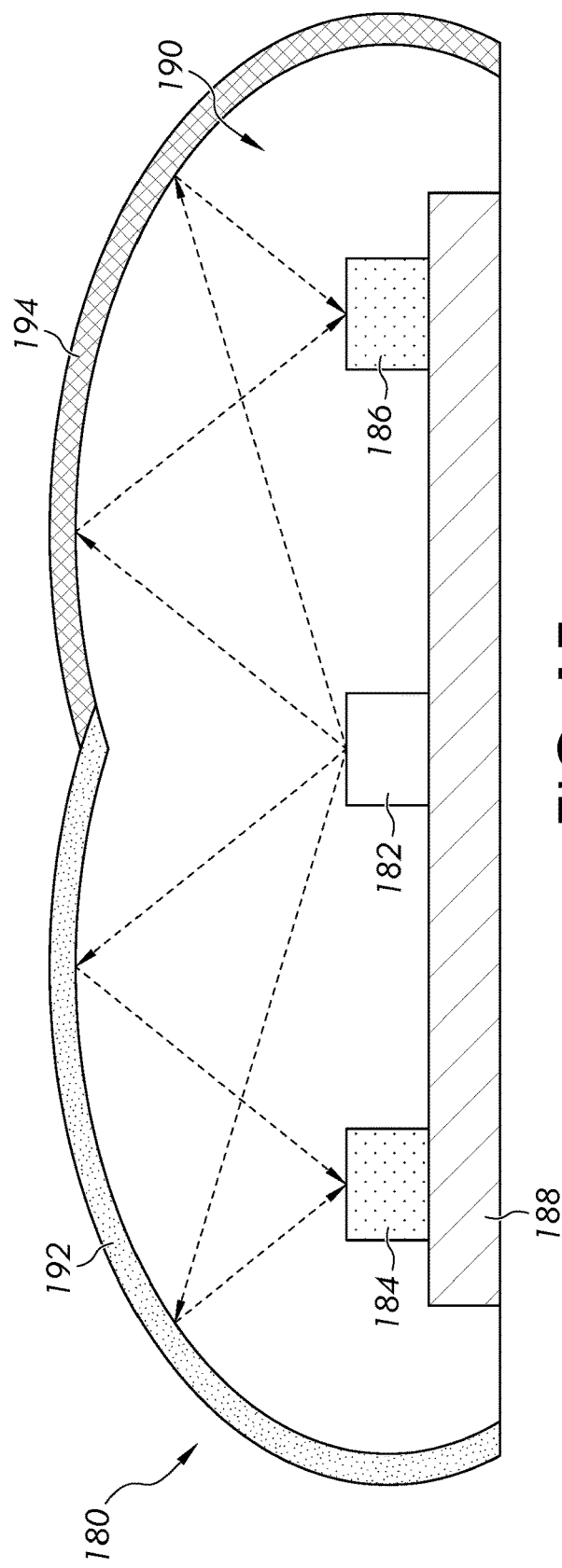
FIG. 15 is a schematic view of an LED sensor having a first LED, a second LED, a third LED, and a reflective film for hydrogen sensing.

FIG. 15 illustrates a schematic view of an LED sensor 180 having a first LED 182, a second LED 184, and a third LED 186. Each of the LEDs is located on an anvil 188 and all are disposed within a structure 190, which is formed as a single package. The LED 182 is a green LED and the LEDs 184 and 186 are yellow LEDs chosen such that 184 and 186 are effective absorbers for light emitted by 182. The structure 190 is shaped into the form of two intersecting semi-ellipsoids which share a focus as previously described. Each of the LEDs 182, 184, and 186 is placed at the focal region of the ellipsoids with the emitter LED 182 located at a point which is the focus shared by the two intersecting semi-ellipsoids to form a compound ellipsoid. One of the semi-ellipsoid package regions is coated with a material layer 192, which in one embodiment is a thin inert mirroring film (e.g. silver) of approximately 300 nm. The other semi-ellipsoid package region is coated with a different material layer 194, which in one embodiment, is a thin reflective film which has a reflectivity that is altered by exposure to hydrogen. Such a film, in different embodiments, is comprised of a thin (approximately 20 nm) outer layer of palladium or a suitable palladium alloy over the top of a thin (approximately 60 nm) layer of a Titanium-Magnesium alloy. This enables the structure to provide both an environmentally sensitive element and a stabilized referencing element. This provides referencing by directing a stable fraction of light from the emitter LED 182 to the two receiver LEDs 184 and 186, by using a film which is environmentally insensitive to focus light onto the LED 184, but which is environmentally modulated (specifically hydrogen sensitive) to focus light onto 186. Thus, the difference between the output signals provided by 184 and 186 provides a composite signal which is stabilized against certain forms of interference or degradation (such as dimming of the emitter LED over time). In other embodiments, two or more of the film layers are differentially sensitive.

Figure 16:
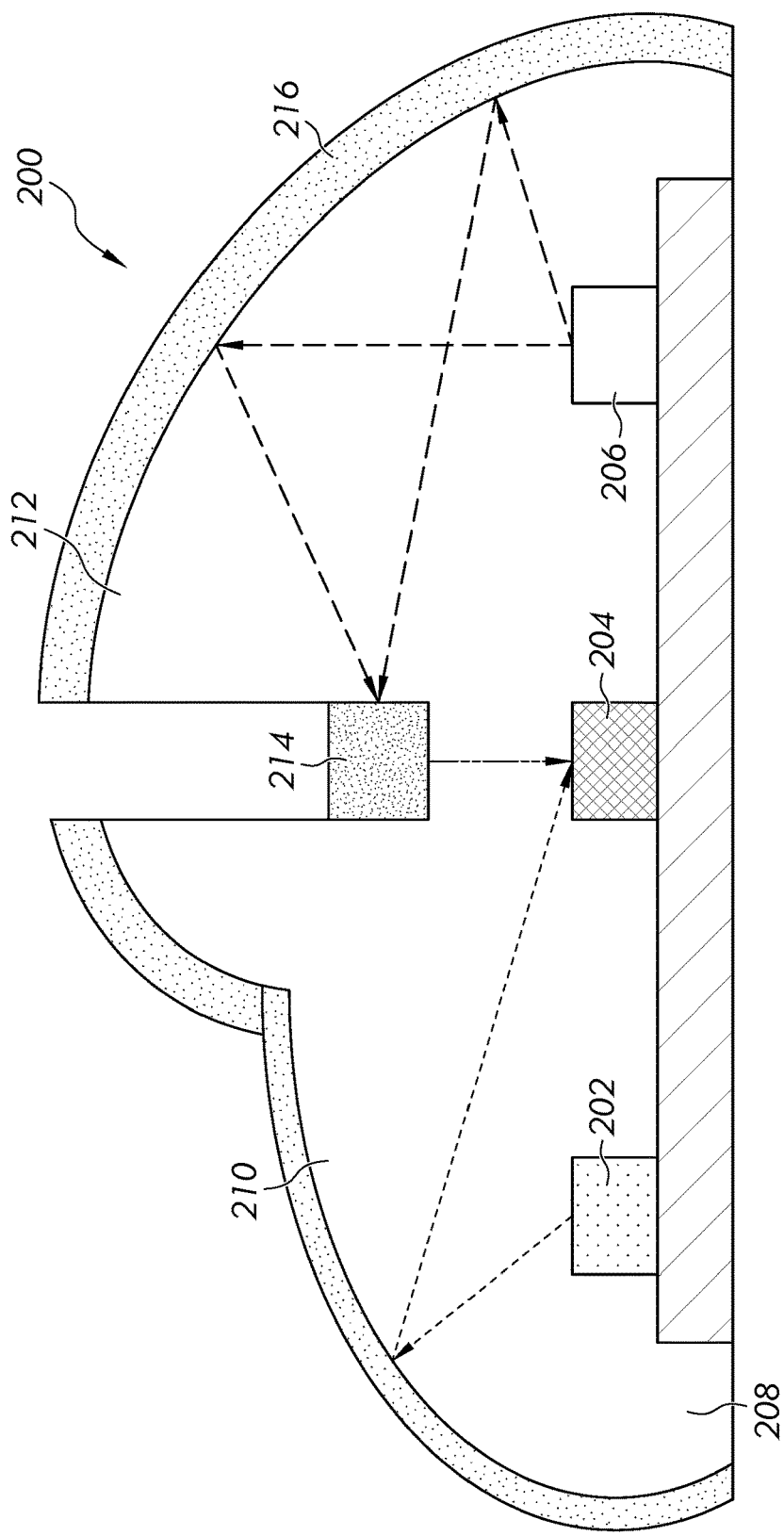
FIG. 16 is a schematic view of an LED sensor having a first LED, a second LED, and a third LED and a luminescent film for sensing oxygen.

FIG. 16 illustrates a schematic view of an LED sensor having a first LED 202, a second LED 204, and a third LED 206. In an exemplary embodiment, each of the three LEDs 202, 204, and 206 are of a different color. LED 202 is red-orange LED. LED 204 is a red LED. LED 206 is a blue LED. A structure 208 is formed in the shape of two intersecting partial-ellipsoids, a first partial-ellipsoid 210 and a second partial-ellipsoid 212. The red-orange LED 202 and the red LED 204 are placed at the focal regions of one of the partial-ellipsoids, partial-ellipsoid 210. The blue LED 206 and a quantity of photoluminescent material 214 are placed at the foci focal regions of the other partial-ellipsoid, partial-ellipsoid 212. A hole is located in the partial-ellipsoid 212 to enable environmental oxygen to efficiently reach the photoluminescent material 214, which is selected from a material of a material system which experiences photoluminescence quenching proportional to the local amount of environmental oxygen, as known in the art As shown in FIG. 16, the of the geometry of partial ellipsoid 210 acts to direct light from 202 to the LED 204 and the geometry of partial ellipsoid 212 acts to direct light from 206 to the material 214 which is in close proximity to LED 204 which enables the photoluminescence of the material 214 in response to illumination from 206 to act as a light source for detection by the LED 204. The foci are not on the surface of the ellipsoids, but are in the interior of the partial ellipsoids, along the central axis of rotation. Ellipsoid 212 includes foci 206 and 214. Ellipsoid 210 has foci 202 and 204. As such, the foci 204 and 214 are located near one another. Light from the LED 206 is efficiently delivered to the material 214 by the semi-ellipsoid geometry and a material layer 216 of a reflective film. The material layer 216 is located at the surface of both of the first semi-ellipsoid 210 and the second semi-ellipsoid 212. This enables the light from the LED 202 to be efficiently delivered to the LED 204 by the local semi-ellipsoid geometry and can be used to serve as an internal referencing source (e.g. for intensity and/or phase shift measurements). In this embodiment, a near-ellipsoidal structure is used in which one focus is the emitter and at the other is an indented feature containing the fluorescent material, and just proximate to this within the package is the sensing element.

In the embodiment of FIG. 16 and others, the material 214 and LED colors are selected to correspond to a coordinating set of characteristics, such that the LED 206 excites the material 214 and is preferably not substantially directly absorbed by LED 204. In another embodiment, the color of LED 202 is selected to be substantially absorbed by LED 204 and the light emitted by material 214 is also substantially absorbed by LED 204. By selecting the colors of each of the LEDs and the type of fluorescent/phosphorescent/photoluminescent material, this type of sensor is useful in many different types of applications including those applied to analytes in both gas and liquid phases.

As described herein, one or more LED junctions of one or more LEDs are encased within a structure comprising a single unitary packaging. Light is emitted from the LED junction and then encounters a material layer, located in close proximity to the structure, which returns light back to the one or more LEDs in a manner which is analyzed to determine the characteristics of the environment (analyte) being tested. This returned light is absorbed by one or more of the LED junctions, and thereby creates a sensible electronic response which is modulated by environmental stimuli. Appropriate electrical test equipment is electrically coupled to the LEDs to enable the LEDs to transmit light (radiation) and to receive light (radiation) for analysis. In some embodiments, these devices are operated utilizing a time-modulated emission signal (e.g. 'blinking'). This can be utilized to improve several performance aspects of these devices including increasing the effective useful lifetime of the LED or reducing the heat generation by the device.

In one or more embodiments, these LED sensors having a packaging housing which encases multiple LEDs and is constructed in such a way as to provide independent electronic connection to these various LEDs within the package so that the signals from the various devices may be directly and unambiguously distinguished.

In still other embodiments, LEDs having differentiated spectrums as emitter-absorber pairs are used. In some embodiments, multiple absorber LEDs with differentiated spectra are provided; for instance, using two absorbers where one has the same (emission) spectrum as the emitter and the other has an (emission) spectrum which is shifted slightly toward the red so that the spectral distribution of the generated signal can be analyzed. Furthermore, in some instances the environment may cause alterations to the spectrum which is returned to the LED sensor—e.g. due to selective absorption, fluorescence, phosphorescence, etc. In such instances, multiple absorbers which have differentiated spectral selectivity are used for characterizing the optical signal. Furthermore, in some embodiments, it may be useful to utilize multiple LEDs to enable the measurement of multiple parameters within the same system e.g. the measurement of local temperature and of a chemical concentration by the same LED sensor package through using different types of LEDs and different types of a material layer to provide a variety of response combinations.

In additional embodiments, the LED sensor package is joined to a conduit which conducts the light to and from a distal location. Such conduits are well known in the art and may include optical fiber, "light pipe", and others. Optical fibers include, but are not limited to, single mode optical fibers, multi-mode optical fibers, bundles of optical fibers, very large diameter optical fibers (often up to multiple mm in diameter). As is well known in the art, there are several methods by which such fibers can be connected to the LED package including lens-coupled mechanical mounts, and gluing the fiber directly to the LED package.

In some embodiments, particularly for sensors based upon specular optical dynamics, the packaging structure may be constructed into a geometry which enables light emitted from the emitter LED to be reflected multiple times from the surface of the packaging structure before being re-focused onto the sensor LED in order to enhance the detectable signal level produced by the system. One such embodiment is illustrated in FIG. 17 which is a schematic view of an LED sensor 220 having a first LED 222, a second LED 224, and a barrier or baffle 226 disposed between the first LED 222 and the second LED 224. Each of the LEDs 222, 224, and the barrier 266 are disposed on a support 228 all of which are enclosed in a contoured structure 230. Each of the LEDs 222 and 224 include LED junctions of a differing color encased within a single packaging of the structure 230. Light emitted from the LED 222 is directed multiple times toward the interior surface of the enclosure 230 which then reflects the emitted light toward the LED 224. Various reflectors of this type are constructed from principles known in the art and one such example is a compound shape formed from the intersection of two concave parabolic reflectors.

In some embodiments, the LED sensor package is constructed to enable the device to measure multiple environmental parameters simultaneously. In one embodiment, this embodiment provides referencing of the device.

In some embodiments, the LED sensor packages are constructed to enable direct internal optical referencing of the device.

In other embodiments, the LED package sensor is constructed so that fluctuations in unmeasured environmental parameters (such as temperature) are calibrated for and/or compensated by the structure of the device. For instance, by utilizing a device which has a symmetric double-ellipsoidal geometry and where one elliptical arm has a film that is responsive to an environmental parameter and the other elliptical arm has a film that is insensitive to said environmental parameter, such an assembly provides built-in referencing characteristics which are symmetric with respect to environmental parameter changes (e.g. temperature). Furthermore, through use of suitable designs with compact geometric forms stabilized by robust materials (e.g. small polymer castings on fiberglass board substrates) effects from environmental parameters such as temperature changes can be minimized.

In still other embodiments, the LED packaging structure is constructed to minimize the amount of light which is produced and re-absorbed within the LED packaging without interacting with the environment. This configuration reduces the baseline optical signal to enable enhanced sensitivity from the device (improved signal-to-baseline). For instance, the embodiment of FIG. 17 includes the barrier 226, which acts as a curtaining barrier between absorber and emitter LED junctions within the packaging. The barrier 226 ensures that light does not travel directly from an emitter to an absorber, without first reflecting off of the surface of the package, which provides the sensitivity. The barrier 226, consequently, maximizes the signal-to-baseline value.

In some preferred embodiments, the LED and packaging structure will be encased within a structure to regulate and/or modify the environment to which the sensor is directly exposed. For instance, the LED and packaging structure may be encapsulated within a membrane to concentrate particular analytes for determination and/or to reduce the presence of contaminants/interferences in the active proximity of the sensor. Various selective membranes are selected to form a physical barrier physically proximate to the sensor device, which selectively enables certain analytes to reach the sensor element while inhibiting the presence of other analytes. In one embodiment for instance, a membrane takes the form of a permeable hydrophobic layer such as a thin layer of teflon, or a self-assembled layer of perfluorosilane onto a silica surface. Thin layers (approximately 0.5 to 20 nm) of silicon oxide are applied to discriminate (e.g. between hydrogen and oxygen permeation). Ion selective membranes are formed, in different embodiments, using layers of from various inorganic (e.g. ion exchange silicate or chalcogenide glasses) or organic (e.g. valinomycin) compositions.

In some embodiments, the external surface of the packaging structure includes micro-structuring or other diffractive elements to induce diffractive effects in the incident light in order to direct some or all of the light onto one or more receiver elements. For instance, the package surface, in one embodiment, is formed as a holographic reflective "lens" (rather than as a structured contour) to direct the path of the light within the package. In some embodiments, this configuration is made using holographic imprinting, as is well known in the art. Such imprinted holograms are formed during casting of the package material. In other embodiments, the imprinted holographic element is comprised partially or completely from materials that are materially responsive so that it may alter the functionality of the holographic e.g. by altering the strength or positioning of the reflection that it creates. In some embodiments, such holographic lens elements are utilized to direct different portions of the spectrum of the light utilized within the system to different spaces within the cell (e.g. onto different sensing LEDs with different spectral sensitivities). This micro-structuring is in contrast with illustrated embodiments described herein in which the exterior surface of the structure is smooth.

In some embodiments, the packaging structure is constructed into a geometry which possesses an optical resonance matching a wavelength utilized by the system (e.g. the wavelength emitted by the LED). In such embodiments the LED or LEDs, which are in electromagnetic contact with the packaging structure, are utilized to populate and detect the resonant optical states associated with the packaging structure.

It will be apparent to those skilled in the art that similar package integration of similar emitter detector pairs (e.g. an LED paired with a photodetector in a single package in proximity to a sensing material/structure) may be utilized to obtain advantages in device simplicity and cost.

While the present disclosure has been illustrated and described in detail in the drawings and foregoing description, the same is to be considered as illustrative and not restrictive in character, it being understood that only certain exemplary embodiments have been shown and described and that all changes and modifications that come within the spirit of the present disclosure are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the present disclosure, the scope being defined by the claims that follow. In reading the claims, it is intended that when words such as "a," "an," "at least one," or "at least one portion" are used there is no intention to limit the claim to only one item unless specifically stated to the contrary in the claim. The term "of" may connote an association with or a connection to another item as well as a belonging to or a connection with the other item as informed by the context in which it is used. The terms "coupled to," "coupled with", and the like include indirect connection and coupling and further include but do not require a direct coupling or connection unless expressly indicated to the contrary. When the language "at least a portion" and/or "a portion" is used the item can include a portion and/or the entire item unless specifically stated to the contrary.

The invention claimed is:

1. A light emitting diode (LED) sensor comprising:
   a first LED junction constructed to emit a radiation;
   a second LED junction constructed to receive a radiation and provide a detectable electronic response responsive to the received radiation;
   a package encapsulating the first LED junction and the second LED junction, wherein the package defines a contoured envelope having a contoured surface; and
   a material located adjacently to the contoured surface, wherein the material is constructed to include a property, wherein the property includes reflecting or absorbing and re-emitting the emitted radiation to the second LED, wherein the property includes reflecting an external radiation and preventing the external radiation from being received by the second LED, wherein the material includes a layer that includes a palladium alloy constructed to change optical reflectivity due to hydrogen absorption, and wherein the LED sensor is configured to detect the presence of hydrogen.

2. The LED sensor of claim 1 wherein the package includes an ellipsoid or partial ellipsoid and the contoured surface defines an ellipsoidal surface.

3. The LED sensor of claim 2 wherein the ellipsoid or partial ellipsoid defines a first foci and a second foci, wherein the radiation emitted from the first foci converges at the second foci and wherein a radiation emitter of the first LED junction is placed at the first foci and a radiation receiver of the second LED junction is placed the second foci.

4. A light emitting diode (LED) sensor comprising:
   a support;
   a first LED device disposed on the support and including a single LED junction constructed to emit a radiation;
   a second LED device disposed on the support and including a single LED junction constructed to receive a radiation and provide a detectable electronic response responsive to the received radiation;
   a structure formed on the support, the first LED device, and the second LED device, wherein the structure defines a contoured surface; and
   a material located adjacently to the contoured surface, wherein the material is constructed to include a property, wherein the property includes reflecting the emitted radiation from the first LED to the second LED, wherein the property includes reflecting an external radiation and preventing at least a portion of the external radiation from being received by the second LED, wherein the material includes a layer constructed to change optical reflectivity due to absorption of an analyte, and wherein the LED sensor is configured to detect the presence of the analyte.

5. The LED sensor of claim 4 wherein the contoured surface and the material cooperate to define an optically sculpted reflector.

6. The LED sensor of claim 5 wherein the first LED emits the radiation having a first wavelength, and the second LED receives the radiation having the first wavelength.

7. The LED sensor of claim 5 wherein the first LED and the second LED each emit a radiation having the same wavelength.

8. The LED sensor of claim 4 wherein the property of the material is adapted to absorb an external radiation and to prevent at least a portion of the external radiation from interfering with a measurement of the analyte.

9. The LED sensor of claim 5 wherein the LED sensor is constructed to detect the presence of a chemical species.

10. The LED sensor of claim 4, wherein the analyte is oxygen, and wherein the sensor is configured to detect the presence of the oxygen.

11. The LED sensor of claim 4, wherein the analyte is a volatile organic compound, and wherein the sensor is configured to detect the presence of the volatile organic compound.

12. A light emitting diode (LED) sensor comprising:
a first LED junction constructed to emit a radiation;
a second LED junction constructed to receive a radiation and provide a detectable electronic response responsive to the received radiation;
a contoured surface; and
a material located adjacently to the contoured surface, wherein the material is constructed to include a property, wherein the property includes reflecting or absorbing and re-emitting the emitted radiation to the second LED, wherein the material includes a color change dye fixed in a gel, and wherein the emitted radiation travels through the gel.

13. The LED sensor of claim 12, wherein the color change dye is a halochromic dye.

14. The LED sensor of claim 12, wherein the color change dye is a thermochromic dye.

15. A light emitting diode (LED) sensor comprising:
a first LED junction constructed to emit a radiation;
a second LED junction constructed to receive a radiation and provide a detectable electronic response responsive to the received radiation;
a contoured surface; and
a material located adjacently to the contoured surface, wherein the material is constructed to include a property, wherein the property includes reflecting or absorbing and re-emitting the emitted radiation to the second LED, and wherein the material includes a chromic sensing material that modulates sensible characteristics of the radiation.

16. The LED sensor of claim 15, wherein the chromic sensing material is halochromic.

17. The LED sensor of claim 15, wherein the chromic sensing material is ionochromic.

18. The LED sensor of claim 15, wherein the chromic sensing material is solvatochromic.

19. The LED sensor of claim 15, wherein the material is constructed to enable permeation of an analyte therethrough to the chromic sensing material.

* * * * *